United States Patent
McKittrick

(10) Patent No.: US 6,984,224 B2
(45) Date of Patent: Jan. 10, 2006

(54) GASTRIC TUBE APPARATUS AND METHOD OF INSERTING GASTRIC TUBE

(76) Inventor: Robert McKittrick, 103 Ambassador Dr., Red Bank, NJ (US) 07709

( * ) Notice: Subject to any disclaimer, the term of this patent is extended or adjusted under 35 U.S.C. 154(b) by 0 days.

(21) Appl. No.: 10/228,178

(22) Filed: Aug. 26, 2002

(65) Prior Publication Data

US 2004/0039350 A1 Feb. 26, 2004

(51) Int. Cl.
*A61M 31/00* (2006.01)

(52) U.S. Cl. ................................. 604/270; 604/910

(58) Field of Classification Search ............. 604/27, 604/28, 35, 39, 43, 45, 48, 257, 258, 263, 604/500, 514, 516, 910, 264, 270
See application file for complete search history.

(56) References Cited

U.S. PATENT DOCUMENTS

| | | | |
|---|---|---|---|
| 4,249,535 A | 2/1981 | Hargest, III | 128/348 |
| 4,315,509 A | 2/1982 | Smit | 128/303 |
| 4,393,873 A | 7/1983 | Nawash et al. | 604/151 |
| 4,588,395 A | 5/1986 | Lemelson | 604/59 |
| 4,613,323 A * | 9/1986 | Norton et al. | 604/43 |
| 4,735,214 A | 4/1988 | Berman | 128/759 |
| 4,739,758 A | 4/1988 | Lai et al. | 128/303 |
| 5,049,138 A | 9/1991 | Chevalier et al. | 604/265 |
| 5,261,898 A | 11/1993 | Polin et al. | 604/328 |
| 5,611,787 A * | 3/1997 | Demeter et al. | 604/270 |
| 5,860,916 A | 1/1999 | Pylant | 600/208 |
| 6,186,985 B1 | 2/2001 | Snow | 604/175 |
| 6,332,877 B1 | 12/2001 | Michels | 604/263 |
| 6,673,058 B2 * | 1/2004 | Snow | 604/506 |

* cited by examiner

*Primary Examiner*—Nicholas D. Lucchesi
*Assistant Examiner*—Mark K. Han
(74) *Attorney, Agent, or Firm*—McCarter & English, LLP

(57) ABSTRACT

A gastric tube apparatus comprising a tube and a weighted leader which are releasbly attached by a material which dissolves in the patient's gastrointestinal tract. The apparatus is introduced into a patient through a nasal opening. After the tube and leader are properly placed in the gastrointestinal tract, the attachment material dissolves and the weighted leader may be removed from the patient, leaving the tube in place for treatment of the patient.

22 Claims, 7 Drawing Sheets

GASTRIC TUBE APPARATUS AND METHOD OF INSERTING GASTRIC TUBE

BACKGROUND OF THE INVENTION

1. Field of the Invention

The present invention relates to a gastric tube apparatus and a method of inserting a gastric tube into a patient's gastrointestinal tract through a nasal opening.

2. Related Art

Nasogastric tubes are used in patient care for introducing and evacuating gases, liquids and solids to and from the gastrointestinal tract. Uses for nasogastric tubes include gastric lavage for foreign matter and poisonings; operative, postoperative, post-traumatic, and resuscitative evacuation of gastrointestinal contents; and enteral feeding and medication administration. Alimentary therapy is also important in the treatment of patients with diseases or conditions that impair intake or digestion of nutrients. Such conditions include oral diseases, paralysis of the masticatory muscles, lengthy unconsciousness, artificial respiration, or psychogenically induced starvation.

Nasogastric tubes are often difficult to negotiate through a patient's anatomy. Typically, generally rigid nasogastric tubes are inserted by force through the nasal passageways, causing the patient considerable discomfort due to tearing and abrasion of the tissues in the nostrils, nasopharynx, hypo-pharynx, and esophagus. If the tubes are inadvertently inserted past the epiglottis and into the trachea instead of the esophagus, the patient's larynx, or vocal cords may also be damaged by the tube.

It is also know to make nasogastric tubes of a soft, pliable material. Although such nasogastric tubes are well tolerated by patients and suitable for general daily use, their use is often limited because they require the patient's 'active' cooperation to be correctly introduced into the patient, e.g., they require complete flexion of the patient's neck with a deep, strong 'swallowing' effort.

Another type of nasogastric tube device is a leader and sinker system. This system is comparatively easy to introduce into patients, requiring little effort on the part of the patient because the leader and sinker assist in guiding the tube through a patient's anatomy. The sinker, or weight, is either permanently attached to the tube, or disconnected before withdrawal of the tube. Among the disadvantages of this system is that if the weight is permanently attached to the tube, the entire apparatus must be retracted through the digestive and nasal tracts which may tear tissue in theses areas and cause discomfort to the patient. If the weight is disconnected before withdrawal, it must pass intact through the entire digestive system.

A further disadvantage of existing nasogastric tube insertion systems is that the trauma that occurs to the digestive system of a patient during insertion and retraction of nasogastric tubes hinders reinsertion of such systems, necessitating insertion of a suitable medical tube system through an alternate route, i.e., surgical insertion. This increases the potential of infection, and increases discomfort and medical costs to the patient.

Accordingly, what is needed, but has not heretofore been provided, is a nasogastric tube which causes minimal patient discomfort. Such an apparatus should minimize damage to the patient's internal tissues during insertion and removal of the apparatus to and from the patient's nasogastric system.

SUMMARY OF THE INVENTION

The present invention provides a gastrointestinal tube apparatus for introduction through the nasal opening of a patient. The apparatus includes an open-ended tube; a weighted leader; and dissolvable attachment means for releasably attaching the tube and leader together. The dissolvable attachment means is made of a material which is soluble or digestible in the gastrointestinal tract of the patient. After placement of the tube into a patient, the dissolvable attachment means dissolves in the stomach of the patient, releasing the leader from the tube. The leader may be removed from the patient, leaving the tube in the patient for treatment. The invention can be used with a single or double lumen tube.

In one embodiment, the dissolvable attachment means comprises one or more bands of soluble or digestible material. The bands encircle the tube and weighted leader, preferably at or near their distal ends. In another embodiment, the dissolvable attachment means comprises a capsule of soluble or digestible material which caps the distal ends of the tube and weighted leader.

The present invention also provides a method of introducing a gastric tube into the gastrointestinal tract of a patient. The method includes attaching a weighted leader to a tube by dissolvable bands or capsule or both, inserting the tube and weighted leader through the nasal opening and into the gastrointestinal system of a patient, allowing the dissolvable bands to dissolve to release the weighted leader from the tube, and removing the weighted leader from the gastrointestinal system of a patient.

BRIEF DESCRIPTION OF THE DRAWINGS

Other important objects and features of the invention will be apparent from the following Detailed Description of the Invention taken in connection with the accompanying drawings in which.

DETAILED DESCRIPTION OF THE INVENTION

The present invention provides a gastrointestinal tube apparatus which is inserted through a patient's a nasal opening. The apparatus includes an open-ended pliable gastrointestinal tube and a weighted leader which are releasably attached side by side, at or near the distal ends by an attachment means made of a dissolvable material. By "distal ends" it is meant the ends of the tube and leader that are inserted into the patient. The dissolvable material is soluble or digestible in a patient's stomach. After the apparatus is introduced through the patient's nasal opening and is placed in the stomach of the patient, the attachment means dissolves to release the leader and weight from engagement with the tube. The leader and weight can then be withdrawn from the gastrointestinal tract, leaving the tube in place for treatment of the patient.

Figure 1:
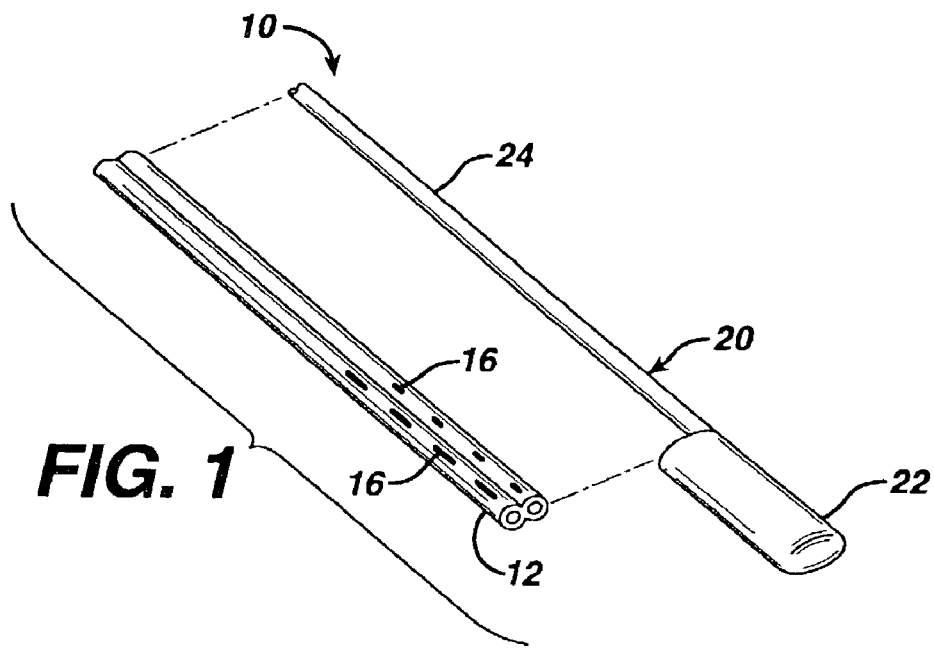
FIG. 1 is an exploded view of the apparatus of the invention showing a double lumen tube and weighted leader.

FIG. 1 shows an exploded view of an embodiment of the nasogastric tube apparatus generally indicated at 10, of the present invention. This apparatus comprises a double lumen tube 12 and a weighted leader 20 which includes weight 22 located at one end of the leader 24. Tube 12 may be provided with an X-ray opaque markings 16 at one end, which markings may be used to differentiate between and identify the lumen of tube 12. Clearly, the invention can be practiced with either a double lumen or a single lumen tube.

Figure 2:
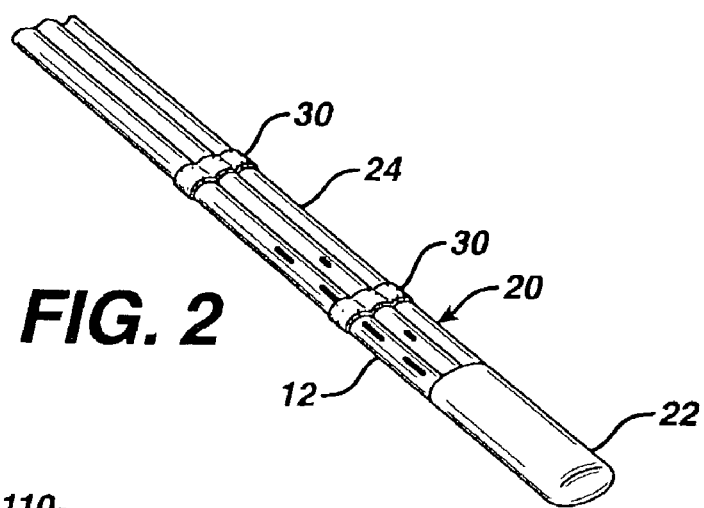
FIG. 2 is a perspective view of the apparatus of the invention showing a double lumen tube, a weighted leader and two dissolvable bands encircling and holding the tube and leader in alignment.

FIG. 2 shows the tube 12 and leader 24 positioned alongside tube 12 with weight 22 positioned at the distal end of tube 12. Preferable, as shown, the leader 24 is attached off-center to one side of the weight 22 and space is provided for the end of the tube 12 to fit against weight 22.

Once the weighted leader 20 and tube 12 are positioned along side each other, dissolvable bands 30 can be used to attach them together. As will be hereinafter discussed in detail, the dissolvable bands 30 are made up of a material that is dissolvable in the body of a patient. The dissolvable bands 30 hold the tube 12 and weighted leader 20 together for insertion of the apparatus into a patient, and then the bands 30 dissolve to permit the weighted leader 20 to be withdrawn from the patient while the tube 12 remains.

Figure 3:
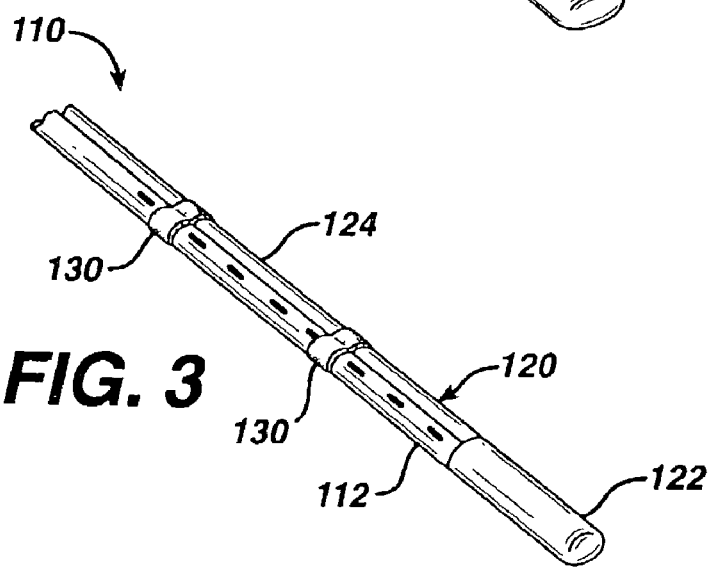
FIG. 3 is a perspective view of the apparatus of the invention showing a single lumen tube, a weighted leader and two dissolvable bands encircling and holding the tube and leader in alignment.
Figure 4:
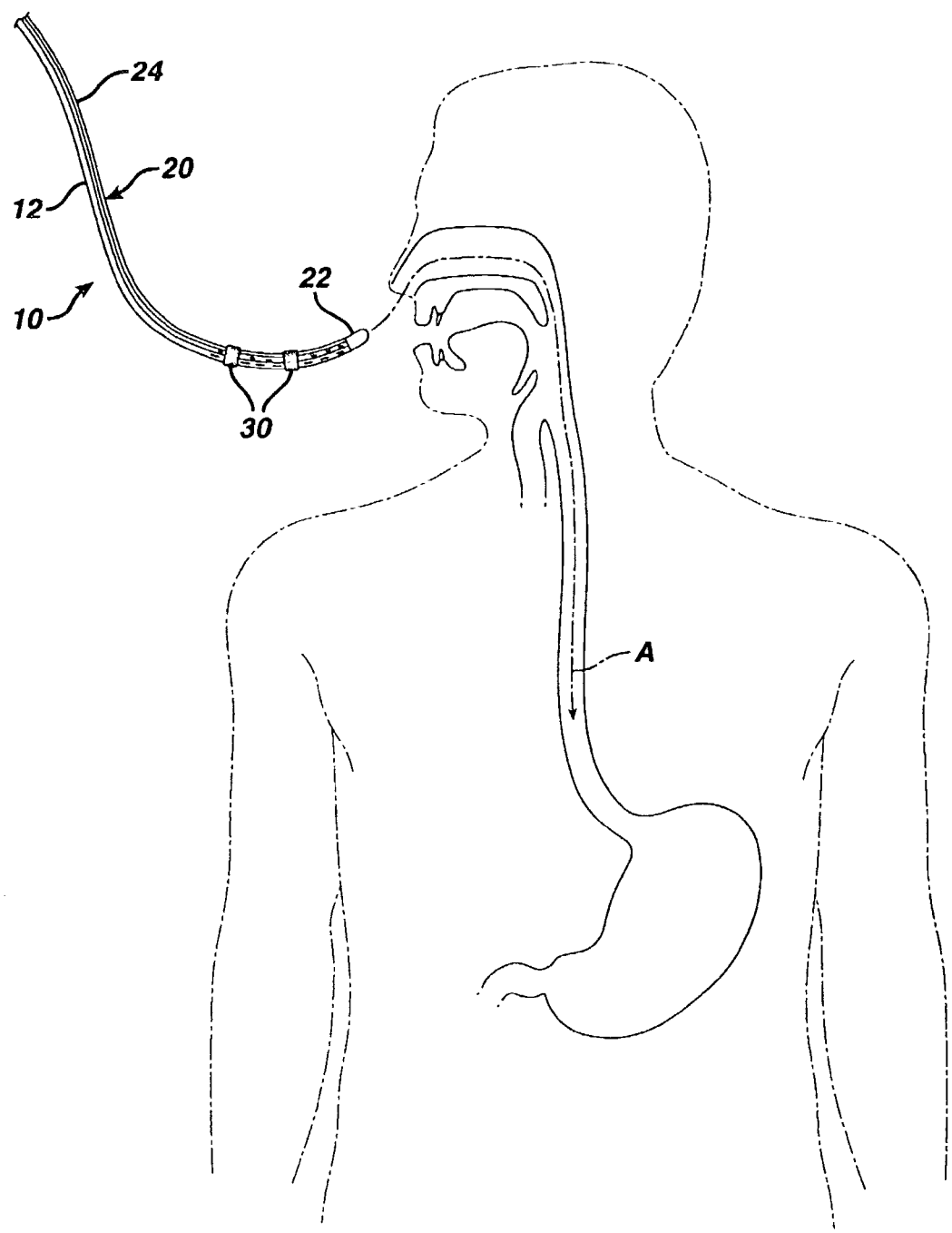
FIG. 4 is a schematic diagram showing a portion of the tube and leader apparatus and a portion of the gastrointestinal tract of a patient and the path of insertion of the apparatus of the invention.

FIG. 3 shows another embodiment of the invention wherein the nasogastric tube apparatus 110 includes a single lumen tube 112 and a weighted leader 120 including weight 122 and leader 124 are held side by side by dissolvable bands 130.

Figure 5:
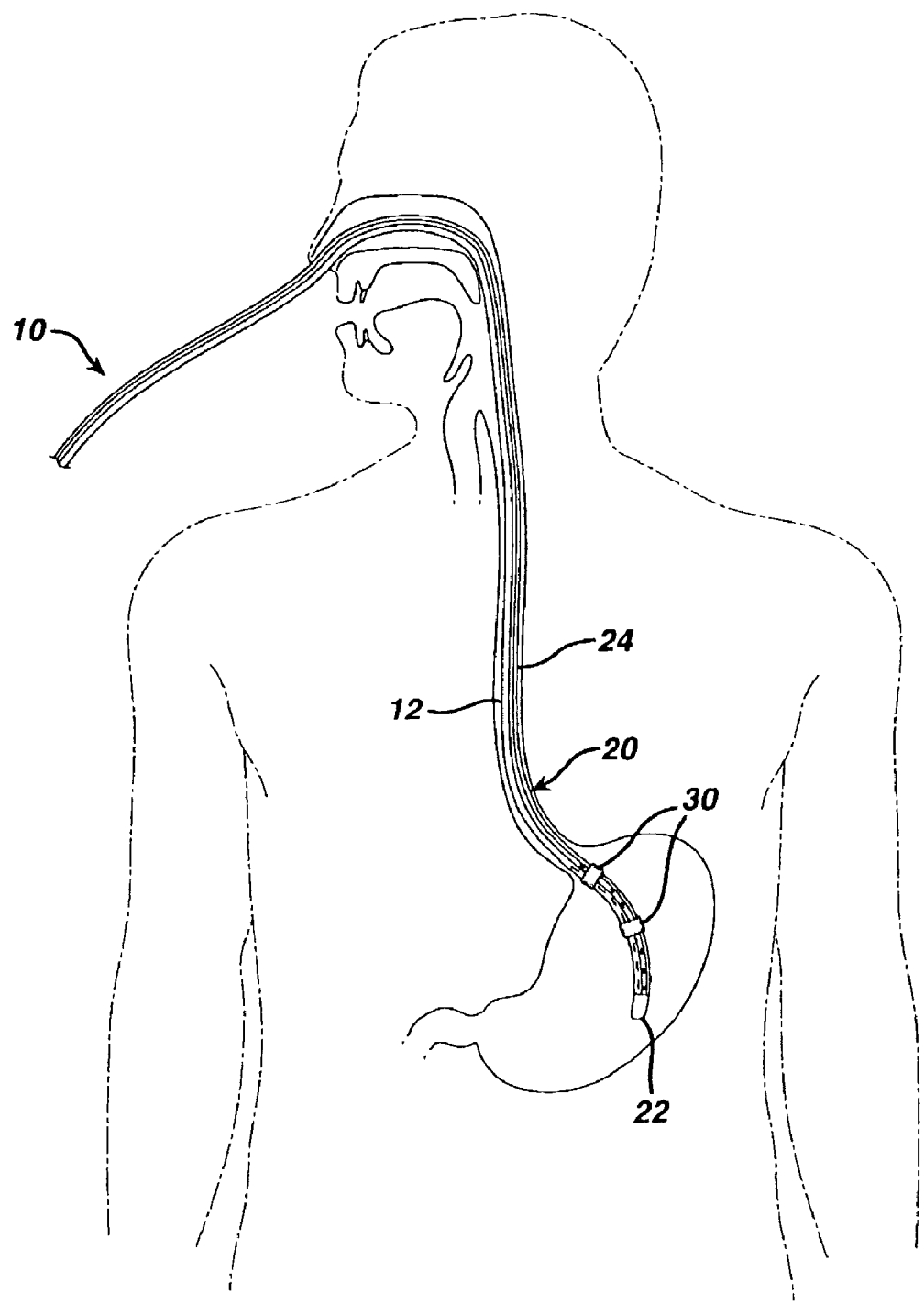
FIG. 5 is a schematic diagram showing the tube and leader attached by dissolvable bands inserted into the stomach of a patient.
Figure 6:
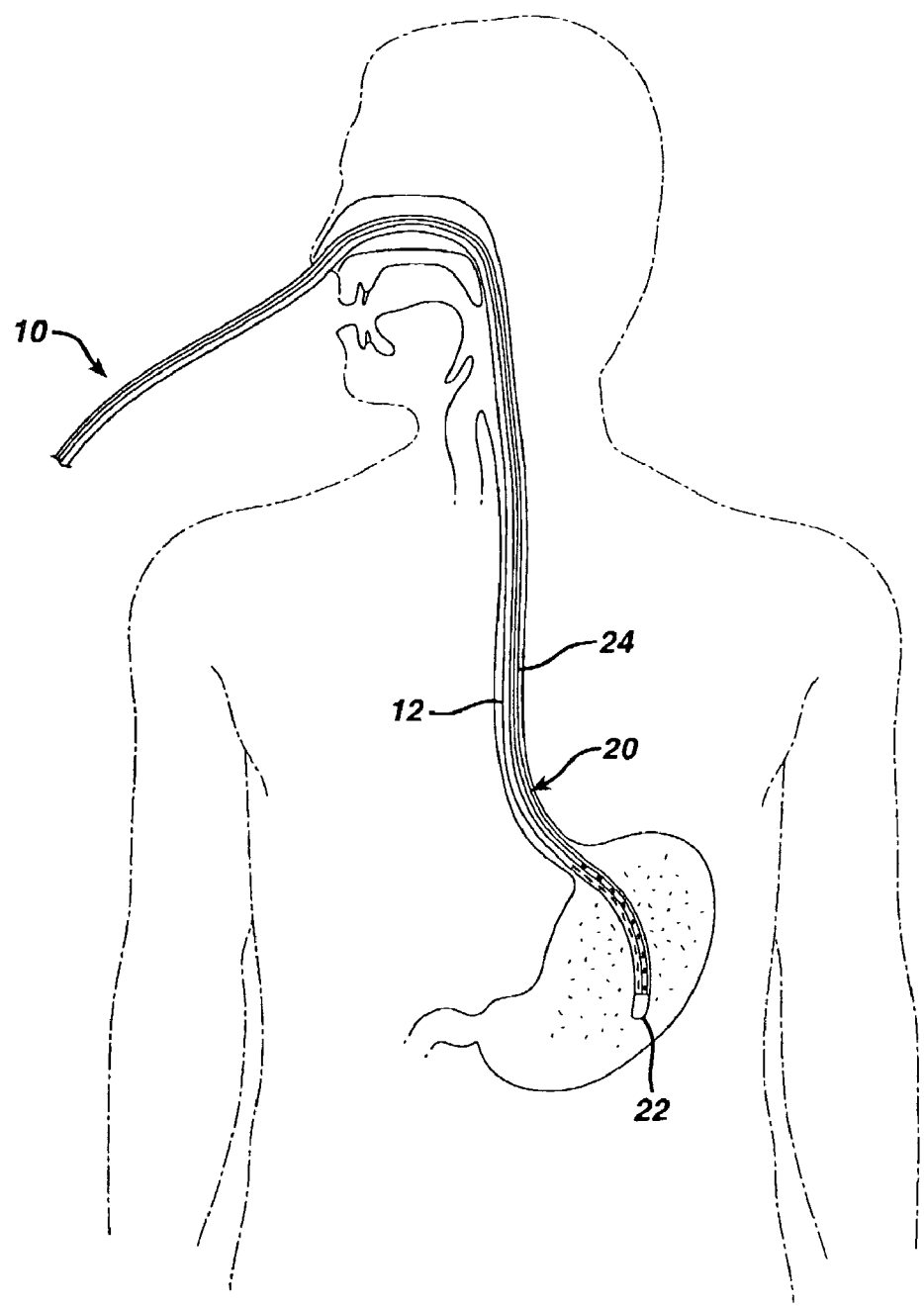
FIG. 6 shows the same view as FIG. 5 with the dissolvable bands dissolved.

FIGS. 4-8 illustrate a method of using the apparatus of the present invention. In operation, the nasogastric tube apparatus 10, comprising tube 12 and weighted leader 20 attached by dissolvable bands 30, is introduced through the patient's nasal opening into the gastrointestinal system. The apparatus may be inserted in a known manner, e.g., by pushing the tube and weighted leader down the nose and throat and into the stomach of the patient in the direction shown by arrow A. Upon placement of the apparatus in the stomach, as shown in FIG. 5, the apparatus is allowed to remain in the patient's stomach or intestine area for a time sufficient to dissolve the attachment bands, typically from about 5 to 20 minutes. As shown in FIG. 6, the bands dissolve and release the tube 12 and weighted leader 20 to allow the weighted leader 20 to be withdrawn from the patient.

Figure 7:
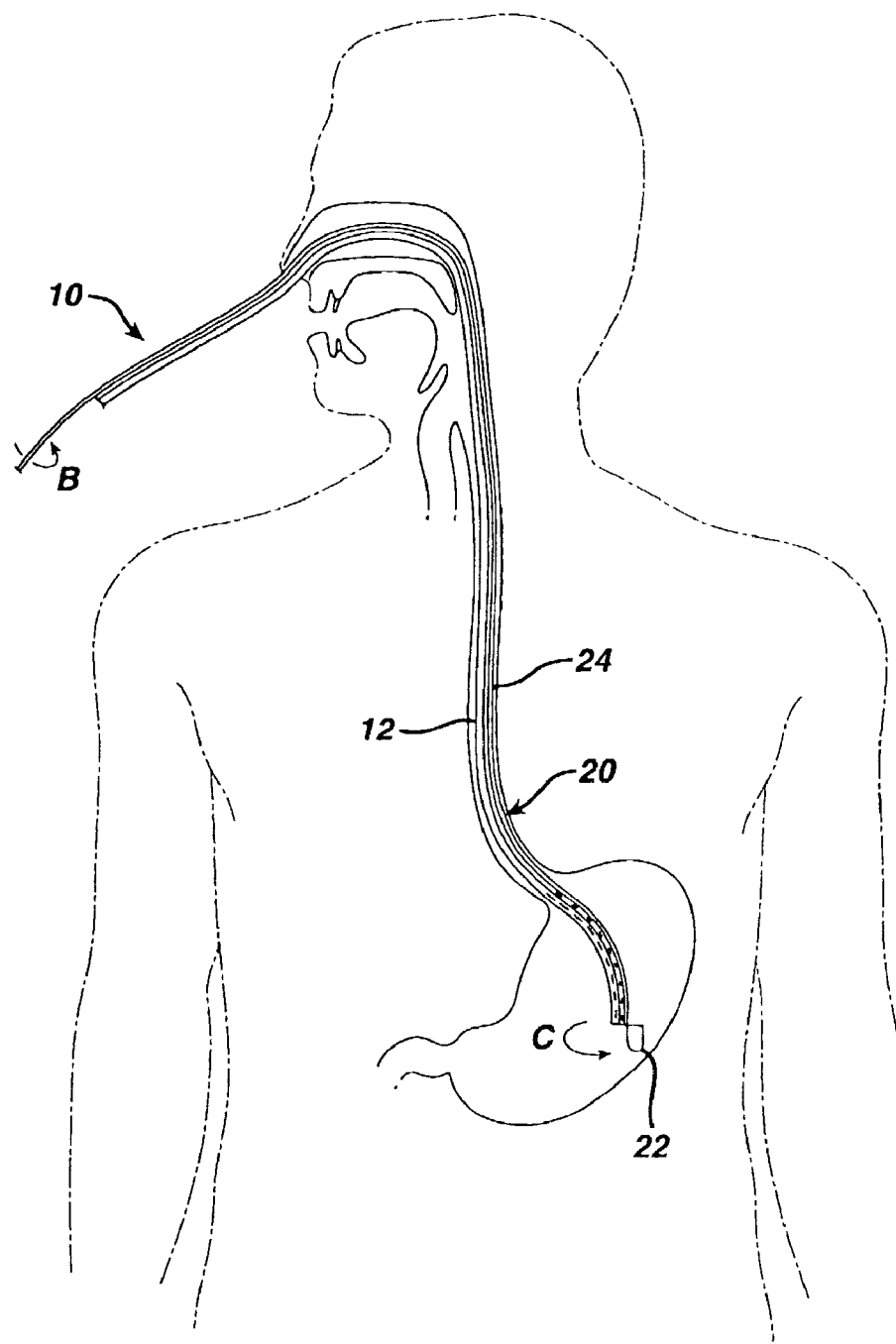
FIG. 7 is a schematic diagram showing the leader twisted to twist the weight away from the end of the tube.

As shown in FIG. 7, to facilitate removal of the weighted leader 20, after the bands dissolve, the leader can be twisted as indicated by the arrow B, to swing the weight 22 away from the end of tube 12 in the direction shown by arrow C.

Figure 8:
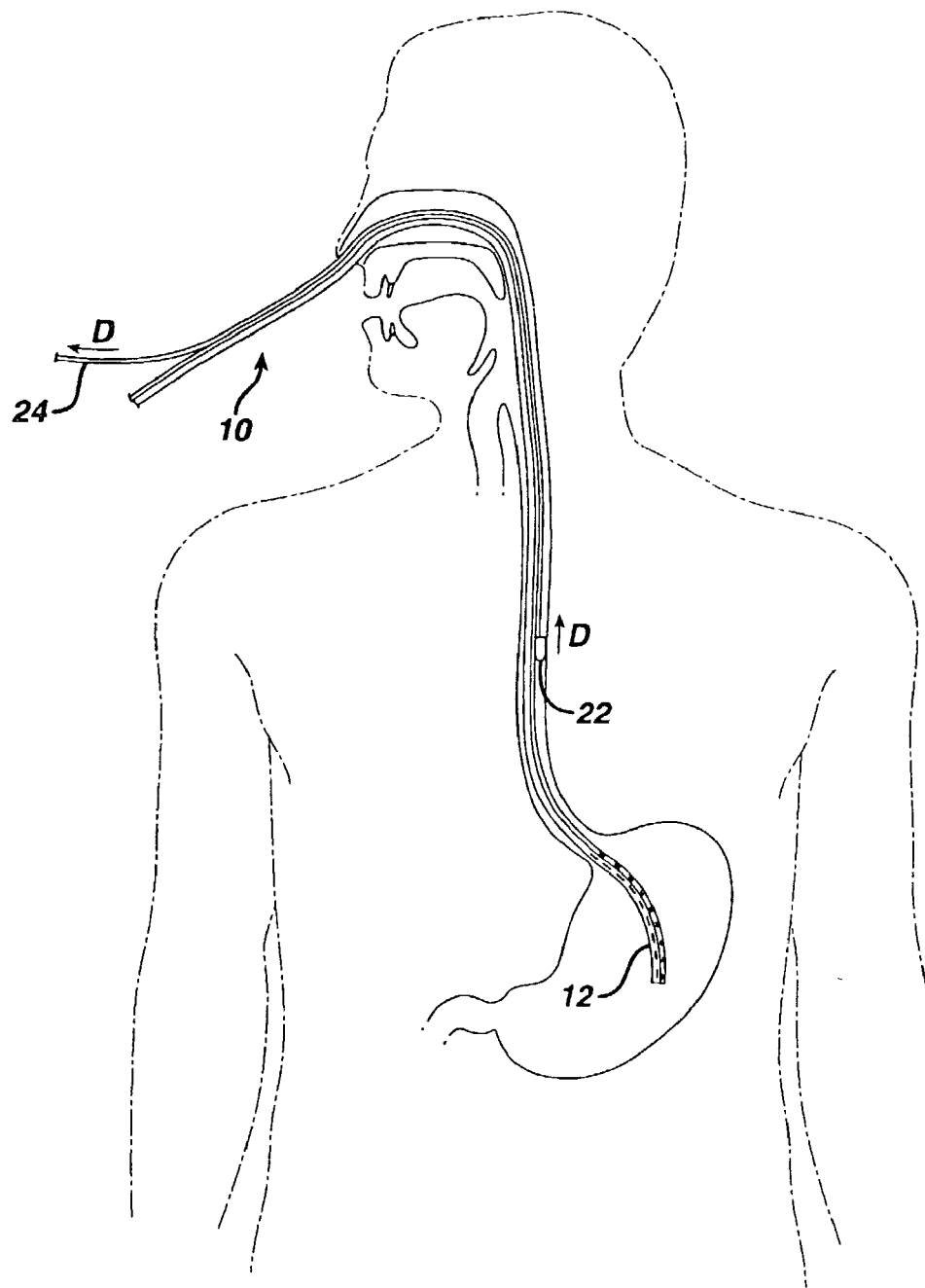
FIG. 8 is a schematic diagram showing the tube in the stomach, and the weighted leader being withdrawn from the gastrointestinal tract of a patient.

As shown in FIG. 8, the weighted leader may then be freely withdrawn from the gastrointestinal system of the patient in the direction of arrow D, with minimal disturbance to the tubing and/or to the patient.

The method of the present invention for inserting a nasogastric tube into the stomach of a patient provides a relatively simple and direct method of guiding, inserting and placing a tube and withdrawing the insertion leader with minimal abrasion and discomfort to the patient.

Figure 9:
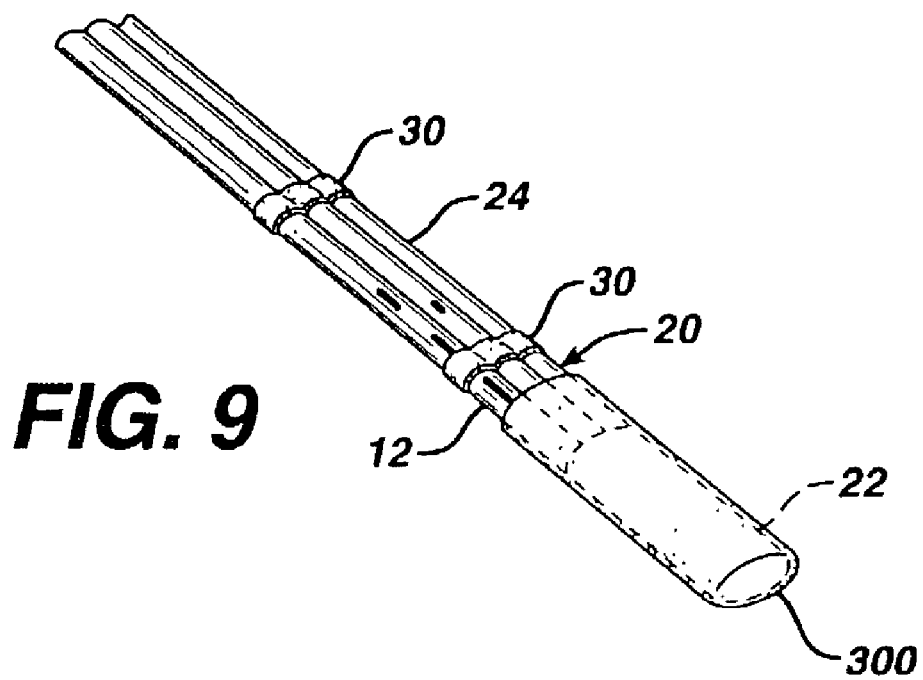
FIG. 9 is a perspective view of another embodiment of the present invention using a capsule to releasably attach the tube and weighted leader.

FIG. 9 shows another embodiment of the nasogastric tube apparatus of the present invention generally indicated at 210. In this embodiment, a capsule 300 is used to retain the weight 222 attached to the tube 212 during insertion of the nasogastric tube apparatus 210 into a patient. Thereafter, the capsule 300 dissolves and releases the attachment of the weighted leader 220 to the tube 212 to permit the withdrawal of the weighted leader 220. The capsule 300 can be used alone or with the dissolvable bands previously discussed. Other releasable attachment means can be used to practice the present invention.

The dissolvable or absorbable bands, capsule or other attachment means is comprised of a material absorbable by or dissolvable in the body of the patient and is pharmacologically safe and non-toxic. Such materials include solidifying substances such as agar, alginic acid, starches, gum arabic, pectin, PVP, methylcellulose or gelatin or other suitable material which will degrade or dissolve in the stomach or intestine of the patient. Typically, the absorbable attachment means is made of gelatin.

The tubes used in connection with the present invention are formed of a suitable pliable material such as is used for catheters or gastrostomy feeding tubes for delivering medicinal and nutritional substances to a patient or for suctioning substances from the patient's gastrointestinal tract. Examples of suitable material include any suitable medical grade plastic commonly used for patient intubation. The tube may further comprise a material that facilitates visualization and placement of the apparatus into the patients gastrointestinal system, for example, an X-ray opaque material running through all or a portion of the length of the tube, preferably at least through the distal end of the tube.

One tube with a single or double lumen may be used, or two tubes may be used with the present invention. Each tube or lumen may independently be used to introduce and evacuate materials into and out of the patient's gastrointestinal system. For example, a first tube may be introduced into a patient for introduction of liquids, solids or medicines into, or for suctioning materials from the gastrointestinal system of a patient. A second, or auxiliary, tube may also be provided for introducing fluids into the gastrointestinal tract, for continuous lavage, or for introducing gases such as oxygen into the respiratory tract during suction through the first tube.

The leader is preferably made of a flexible slender rod or line which may be enlarged at the distal end providing a heavier weighted portion. Alternatively, the weight may be formed separately from the leader of preferably the same or similar material and attached to the leader by known means suitable to maintain a permanent attachment while the apparatus is in use. The weighted leader is typically made of a metal, such as stainless steel, but can be made of other metals or other materials as known in the art or hereinafter developed. The leader is preferably coated with an acid resistant coating such as plastic or resin that will reduce or inhibit corrosion of the metal, particularly upon exposure to stomach fluids. The end of the weight may have rounded edges to minimize trauma or abrasion of the surfaces of the nasogastric system when the apparatus is introduced into the patient. The coating may also provide the leader and weight with a more slippery or smoother surface to facilitate introduction thereof through the nasal opening into the patient's gastrointestinal tract. Similar design considerations may be given to the proximal end of the weight to facilitate removal thereof. The leader typically has a length substantially the same as that of the gastrointestinal tube.

Typically the length of the apparatus of the invention will be such that it fits comfortably through the patient's nasal opening and gastrointestinal tract. The diameter of the apparatus is substantially uniform to fit comfortably through the passages of the nose, pharynx, esophagus and endotracheal tubes and into the stomach.

Having thus described the invention in detail, it is to be understood that the foregoing description is not intended to limit the spirit and scope thereof. What is desired to be protected by Letters Patent is set forth in the appended claims.

What is claimed is:

1. A gastrointestinal tube for nasal insertion into a patient comprising:
    an open-ended tube;
    a weighted leader; and
    dissolvable attachment means for releasably attaching the tube and leader together.

2. The apparatus of claim 1 wherein the attachment means comprises a band of soluble or digestible material which encircles the tube and weighted leader at or near the distal ends thereof.

3. The apparatus of claim 1 wherein the attachment means is a capsule of soluble or digestible material which caps the ends of the tube and weighted leader.

4. The apparatus of claim 3 wherein the attachment means further comprises a band of soluble or digestible material which encircles the tube and weighted leader at or near the distal ends thereof.

5. The method of introducing a gastric tube into a patient's gastrointestinal tract through a nasal opening comprising:
    attaching a leader with a weight to a tube by dissolvable bands;
    inserting the tube and weighted leader through the nasal opening and into the gastrointestinal tract of a patient;
    allowing the dissolvable bands to dissolve to release the weighted leader from the tube; and
    removing the weighted leader from the gastrointestinal tract of a patent.

6. The method of claim 5 further comprising twisting the leader to twist the weight away from the tube prior to removing same.

7. A method of introducing a gastric tube into a patient's gastrointestinal tract through a nasal opening comprising:
    attaching a leader with a weight to a tube by a dissolvable capsule;
    inserting the tube and weighted leader through the nasal opening and into the gastrointestinal tract of a patient;
    allowing the dissolvable capsule to dissolve to release the weighted leader from the tube; and
    removing the weighted leader from the gastrointestinal tract of a patient.

8. The method of claim 7 further comprising twisting the leader the weight away from the tube prior to removing same.

9. A gastrointestinal tube for nasal insertion into a patient comprising:
    an open-ended tube;
    a weighted leader; and
    a dissolvable attachment band for releasably attaching the tube and leader together.

10. The gastrointestinal tube of claim 9 further comprising a second dissolvable attachment band attaching the tube and leader together.

11. The apparatus of claim 10 wherein the dissolvable attachment bands comprise a band of soluble of digestible material which encircle the tube and weighted leader at or near the distal ends thereof.

12. The apparatus of claim 9 further comprising a capsule of soluble or digestible material which caps of the tube and weighted leader.

13. A gastrointestinal tube for nasal insertion into a patient comprising:
    an open-ended tube;
    a weighted leader; and
    a dissolvable attachment capsule for releasably attaching the tube and leader together.

14. The gastrointestinal tube of claim 13 further comprising a dissolvable attachment band attaching the tube and leader together.

15. A gastrointestinal tube for nasal insertion into a patient comprising:
    a gastrointestinal tube having an open end;
    a leader with a weight at an end thereof; and
    a dissolvable attachment for attaching the leader and tube, the weight positioned proximate the open end of the tube.

16. The apparatus of claim 15 wherein the attachment means comprises a band of soluble or digestible material which encircles the tube and weighted leader at or near the distal ends thereof.

17. The apparatus of claim 15 wherein the attachment means is a capsule of soluble or digestible material which caps the ends of the tube and weighted leader.

18. The apparatus of claim 17 wherein the attachment means further comprises a band of soluble or digestible material which encircles the tube and weighted leader at or near the distal ends thereof.

19. A gastrointestinal tube for nasal insertion into a patient comprising:
    an open-ended tube;
    a weighted leader; and
    a dissolvable attachment means for a releasably attaching the tube and the leader together;
    wherein, the tube and the weighted leader are inserted into a patient and the leader is used to remove the weight from the patient after the attachment means are dissolved.

20. The apparatus of claim 19 therein the attachment means comprises a band of soluble or digestible material which encircles the tube and weighted leader at or near the distal ends thereof.

21. The apparatus of claim 19 wherein the attachment means is a capsule of soluble or digestible material which caps the ends of the tube and weighted leader.

22. The apparatus of claim 21 wherein the attachment means further comprises a band of soluble or digestible material which encircles the tube and weighted leader at or near the distal ends thereof.

* * * * *